United States Patent [19]

Ohara et al.

[11] Patent Number: 5,801,025
[45] Date of Patent: Sep. 1, 1998

[54] METHOD FOR PRODUCING L-LACTIC ACID WITH HIGH OPTICAL PURITY USING BACILLUS STRAINS

[75] Inventors: Hitomi Ohara; Masahito Yahata, both of Kyoto, Japan

[73] Assignee: Shimadzu Corporation, Kyoto, Japan

[21] Appl. No.: 738,289

[22] Filed: Oct. 25, 1996

[30] Foreign Application Priority Data

Oct. 27, 1995 [JP] Japan .................................. 7-280660
Oct. 27, 1995 [JP] Japan .................................. 7-280661

[51] Int. Cl.$^6$ .................................. C12P 7/56; C12P 7/42
[52] U.S. Cl. .................................. 435/139; 435/146; 435/252.5
[58] Field of Search .................................. 435/146, 139, 435/252.5

[56] References Cited

U.S. PATENT DOCUMENTS 5,002,881  3/1991  Van Nispen et al. .................. 435/139
5,079,164  1/1992  Kirkovits et al. ..................... 435/252.5

OTHER PUBLICATIONS

Shcherbakov M., Prikl. Biokhim. Mikrobiol. 4(3): 243–51 (1968).

Heriban V. et al, Kvasny Prum. 38(10): 293–7 (1992).

ATCC Catalog of Bacteria & Bacteriophays pp. 42,43,56,64.

*Primary Examiner*—Sandra E. Saucier
*Attorney, Agent, or Firm*—Birch, Stewart, Kolasch & Birch, LLP

[57] ABSTRACT

A method for producing an L-lactic acid with an optical purity of not lower than 70% comprising the steps of:(a) cultivating a microorganism of the genus Bacillus, in particular, *Bacillus cereus* and *Bacillus thuringiensis*, capable of producing an L-lactic acid with an optical purity of not lower than 70% from an assimilable carbon source; and (b) collecting an L-lactic acid with an optical purity of not lower than 70% from the culture.

3 Claims, No Drawings

METHOD FOR PRODUCING L-LACTIC ACID WITH HIGH OPTICAL PURITY USING BACILLUS STRAINS

BACKGROUND OF THE INVENTION

1. Field of the Invention

The present invention relates to a method for producing L-lactic acid with a high optical purity using strains of certain Bacillus species. More specifically, it relates to a method for producing L-lactic acid with a high optical purity at low cost. The present invention also relates to a method for simultaneous production of L-lactic acid with a high optical purity and a pesticidal toxin.

2. Discussion of the Related Art

L-lactic acid has been used as a starting material for producing a polylactic acid, a biodegradable plastic. L-lactic acid has found its application in various fields including food and pharmaceuticals, brewing, tanning and optical materials. The pesticidal toxin produced by the bacteria of the present invention has attracted attention because it, unlike conventionally used agricultural chemicals, is harmless to humans and animals.

When lactic acid is used as the starting material in the production of polylactic acid, the higher the optical purity of the starting lactic acid, the higher the degree of crystallization of the polymer produced, as reported by Kulkarni et al.[Biodegradable poly(lactic acid)polymers: Kukarni, R. K., Moore, E. G., Hegyeli, A. F., and Leonard, F., J. Biomed. Mater. Res., 5, 169–181 (1971)] and by Ohara [Poly-L-lactic acid as biodegradable plastic: Ohara, H., Biosci. Indust., 52, 642–644 (1994)]. The polylactic acid with a high degree of crystallization is suitably used for stretched films and fibers.

Highly pure L-lactic acid is usable as liquid crystals, as mentioned by Sato et al.[Properties of the ferroelectic polymer liquid crystals containing a chiral lactic acid derivative group: Sato, K., Eguchi, T., Toshida, Y., Yoshinaga, K., and Takasu, Y., Polymer preprints, Japan, 39, 1962–1964 (1990)] and by Yoshinaga et al. [Properties of the ferroelectric polymer liquid crystals containing a chiral lactic acid derivative group (II): Yoshinaga, K., Eguchi, T., Sato, K., Toshida, Y., and Takasu, Y., Polymer preprints, Japan, 39, 1962–1964 (1990)].

The Food and Agriculture Organization of the United Nations (FAO) and the World Health Organization (WHO) recommend that lactic acid fed to infants be L-lactic acid [FAO and WHO toxicological evaluation of certain food additives with a review of general principles and of specifications, p.23, WHO, Geneva (1974)].

Thus, L-isomer of lactic acid is useful and required to have a high optical purity.

L-lactic acid has conventionally been produced by fermentation methods, which include:

(1) A method using *Streptococcus faecalis* [Lactic acid production by a filter-bed-type reactor: Ohara, H., Hiyama, K., and Yoshida, T., J. Ferment. Bioeng. 76, 73–75 (1993)];

(2) A method using *Lactobacillus helvetics* [Continuous production of lactic acid from whey permeate by *Lactobacillus helvetics* in two chemostats in series: Aeschlimann, A., Di Stasei, L., and von Stockar, U., Enzyme Microbiol. Technol., 12, 926–932];

(3) A method using *Lactobacillus amylovorus* [A new starch-hydrolyzing species from swine waste-com fermentation: Nakamura, L. K. and Crowell, C. D., Div. Ind. Microbiol. 20, 531–540 (1979)];

(4) A method using *Lactobacillus delbruekii* [Production of L-lactic acid with immobilized *Lactobacillus delbruekii*: Stenroos, S. L., Linko, Y. Y., and Linko, P, Bacteriol. Lett. 4, 159–164 (1982)]; and (5) A method using *Lactococcus lactis* [Computer simulation of L-lactate batch fermentation applying the enzyme inactivation scheme: Ishizaki, A. and Kobayashi, G., J. Ferment. Bioeng. 70, 139–140(1990)].

The above (1) to (5) are methods for producing L-lactic acid with lactic acid bacteria. These lactic acid bacteria are highly auxotrophic, and requires expensive culture media as reported by Boer et al. [D-Lactic acid production by suspended and aggregated continuous cultures of *Bacillus laevolacticus*: Boer, J. P. de, Mattos, M. J. T. de, and Neijssel O. M., Appl. Microbiol. Biotechnol., 34, 149–153 (1990)]. Expensive media increase the cost of L-lactic acid products.

In view of the above situation, methods utilizing bacteria other than lactic acid bacteria were reported. For example, Tamada, et al. described a method using *Rhizopus oryzae* [Production of L(+)-lactic acid by immobilized cells of *Rhizopus oryzae* with polymer supports prepared by γ ray induced polymerization: Tamada, M., Bagum, A. A., and Sadai, S., J. Ferment. Bioeng. 74: 379–383 (1992)]. In this method, the duration of fermentation is as long as 40 to 50 hours, resulting in poor production efficiency.

As for the D-isomer of lactic acid, there is a report on a method for producing the isomer utilizing *Bacillus laevolactis* in the above-mentioned reference (Appl. Microbiol. Biotechnol., 34: 149–153). But this method is not suitable for the production of L-lactic acid.

JP-A-58-40093, JP-B-60-6200, and USP 5079164 disclose methods for producing L-lactic acid using *Bacillus coagulans*. *Bacillus coagulans*, however, is a highly auxotrophic bacteria as compared to the bacteria used in the present invention and, therefore, requires expensive culture media. Also, the optical purity of L-lactic acid produced by the species is lower(<70%) than that produced by the bacterial strains of the present invention. Also, there have been no known strains of *Bacillus coagulans* which can produce a pesticidal toxin.

Although a production method utilizing *Bacillus coagulans* is disclosed in JP-A-3-27291, there is no disclosure at all about the type of isomer produced (L or D), and optical purity of the lactic acid produced. In JP-A-2-76592, a method for producing lactic acid utilizing Bacillus strains is disclosed, but no disclosure is found in the description about actual production of L-lactic acid utilizing a Bacillus strain.

SUMMARY OF THE INVENTION

The first object of the present invention is to provide a solution to the above problems by providing a method for producing L-lactic acid with a high optical purity using a specific bacterial strain which belongs to the genus Bacillus.

The second object of the present invention is to provide a method for simultaneously producing L-lactic acid with a high optical purity and a pesticidal toxin using a certain bacterial strain of the genus Bacillus, thereby reducing the total cost for producing a highly pure L-lactic acid.

The third object of the present invention is to provide a method for producing L-lactic acid with a high optical purity using a novel Bacillus strain which is capable of producing L-lactic acid at a high optical purity of not lower than 95%.

The fourth object of the present invention is to provide a novel Bacillus strain which is capable of producing L-lactic acid at a high optical purity of not lower than 95%.

In the first embodiment of the present invention, L-lactic acid with an optical purity of not less than 70% is produced at low production cost by cultivating at least one strain belonging to the genus Bacillus selected from the group consisting of *Bacillus anthracis, Bacillus cereus, Bacillus thuringlensis,* and *Bacillus larvae, Bacillus lentimorbus, Bacillus popilliae,* and *Bacillus sphaericus* strains. The Bacillus strains used in this embodiment are capable of producing L-lactic acid from assimilable carbon sources.

In the second embodiment of the present invention, L-lactic acid with a high optical purity of not less than 70% and a pesticidal toxin are obtained at the same time by cultivating at least one strain selected from the group consisting of *Bacillus thuringiensis, Bacillus larvae, Bacillus lentimorbus, Bacillus popilliae,* and *Bacillus sphaericus* strains. The bacterial strains used in this embodiment are capable of producing L-lactic acid and a pesticidal toxin from an assimilable carbon source.

The third embodiment of the present invention is characterized in that an L-lactic acid with an optical purity of not lower than 95% is produced at low production cost by cultivating a strain of Bacillus sp. SHO-1 (FERM BP-5682) which is capable of producing L-lactic acid from assimilable carbon sources.

The fourth embodiment of the present invention is a microbiologically novel Bacillus strain which is capable of producing L-lactic acid at a high optical purity of not lower than 95%.

DETAILED DESCRIPTION OF THE INVENTION

The present invention will hereinafter be described in detail.

The strains of the genus Bacillus used in the first embodiment of the present invention include strains belonging to *Bacillus anthracis, Bacillus cereus, Bacillus thuringiensis, Bacillus larvae, Bacillus lentimorbus, Bacillus popilliae* and *Bacillus sphaericus* which are capable of producing L-lactic acid with an optical purity of not lower than 70%. By the use of the strains of the genus Bacillus as above, L-lactic acid can be produced at a high optical purity of not less than 70%. Among these microbes, *Bacillus anthracis, Bacillus cereus,* and *Bacillus thuringiensis* are so closely related that bacteriological differentiation among these species is difficult as described on page 1113 of Bergey's Manual of Systematic Bacteriology Vol.2 (1986), P. H. A. Sneath (ed.), Williams & Wilkins. These three species share a common characteristic that they are positive to Egg-yolk lecithinase reaction.

The strains of the genus Bacillus which are used in the second embodiment of the present invention and which permit concurrent production of L-lactic acid with a high optical purity and a pesticidal toxin include *Bacillus thuringiensis, Bacillus larvae, Bacillus lentimorbus, Bacillus popilliae,* and *Bacillus sphaericus* strains.

In the third embodiment of the present invention, L-lactic acid with a high optical purity of not lower than 95% can be produced using Bacillus sp. SHO-1 (FERM BP-5682), a novel strain of the genus Bacillus. The details of the novel strain are described in the fourth embodiment below.

In the fourth embodiment, the strain Bacillus sp. SHO-1 (FERM BP-5682) is used. This strain is capable of producing L-lactic acid at a significantly high optical purity. This strain was isolated from cow's milk by the inventors according to the following procedures: a sample of milk is streaked on a BCP (Bromocresol Purple) count plate agar (Nissui Pharmaceutical, Co., Ltd.), which is then placed in a BBL GasPak and incubated at 34° C. for 24 hours. The color of agar plate around the colonies producing an acid is changed from purple to yellow. The bacteria in the colonies showing the color change are picked up with a platinum loop and streaked again on a fresh BCP count plate agar. This process is repeated 2 to 5 times. The colonies thus screened are then transferred to a 10 ml liquid medium containing 2% glucose, 1% yeast extract, 1% peptone, and 3.5% dipotassium phosphate (adjusted with HCl to pH 7.0), and incubated in a GasPak at 34° C. for 24 hours. The target strain Bacillus sp. SHO-1 can be obtained by analyzing the culture liquid for the optical purity of the L-lactic acid contained therein and selecting the one producing L-lactic acid at a high optical purity. The analysis of the optical purity of L-lactic acid in the liquid culture medium is carried out according to the methods described in Examples of the present specification. The bacterial strain obtained is essentially pure.

The bacteriological properties of Bacillus sp. SHO-1 are as follows:

(a) Morphology Shape: rod Size: 5 μm in length×2 μm in width Motility: +Spore formation: +
Sporangium: no swelling Shape: ellipse Location: intermediary to subterminal (b) Physiology Gram staining: +Catalase activity: +Egg-yolk lecithinase reaction: +Indol production: −Voges-Proskauer test: +Assimilable sugars:
Glucose: +Maltose: +Fructose: +Saccharose: −Lactose: +Raffinose: −Mannitol: −

The above properties indicate that the strain SHO-1 belongs to the genus Bacillus.

The strain SHO-1 does not differ from known Bacillus strains with respect to the physiological properties as listed above. However, as demonstrated in Example, this strain has a capability of producing L-lactic acid at a significantly high optical purity. Therefore, since the strain SHO-1 is not identical to any known Bacillus strains in this respect, this strain is considered to be a novel strain which belongs to the genus Bacillus.

The strain Bacillus sp. SHO-1 has been deposited Sep. 27, 1996 under accession number FERM BP-5682 at the National Institute of Bioscience and Human-Technology, Agency of Industrial Science and Technology, Ministry of International Trade and Industry.

The strain Bacillus sp. SHO-1 is very useful because it is less auxotrophic as compared with other lactic acid bacteria and *Bacillus coagulans,* and can grow on a less expensive medium, thereby enabling the production of L-lactic acid with a high optical purity at low cost.

As to carbon sources, any sugars may be used in the first and second embodiments of the present invention, as long as they are assimilable sugars. In addition to glucose, sucrose, maltose, fructose, lactose, mannitol, and starch may be used. The preferred carbon sources used in the third embodiment include glucose, maltose, fructose, and lactose. The concentration of the sugar in culture media is usually in the range of from 2 to 15% by weight.

Also, inexpensive materials, such as peptone, cheese whey, corn steep liquor and yeast extract, can be used as side starting materials. The concentration of these side starting materials in culture media is normally about 0.1 to 2% by weight. The peptone concentration in culture media, in particular, is normally about 0.5 to 2% by weight.

Also, the culture media may contain inorganic salts, such as potassium phosphate and ammonium phosphate, pH regulators, such as caustic soda, hydrochloric acid and various buffers, magnesium compounds, manganese compounds and others.

Bacterial cells are normally cultivated by the batch-wise method using an STR (stirred tank reactor) but may be cultivated by the continuous method using a CSTR (continuous tank reactor). Also, the cells may be immobilized in calcium alginate, carrageenan or photosetting resin, or may be cultivated using a membrane type or electrodialysis type reactor. For example, a membrane type reactor (dialysis type) are described by Coulman et al. (Applied Environmental Microbiology, 34, 725–732 (1977)), by Stieber and Gerhardt (Biotechnology and Bioengineering, 23, 523–534 (1981)), and in other publications. A cross-flow type membrane type reactor is described by Major and Bull (Biotechnology and Bioengineering, 34, 592–599 (1989)), and in other publications.

Although depending on the cells used, pH and temperature for cultivation in the first, second and third embodiments of the present invention are normally 6.0 to 8.0 and 25 to 40° C., respectively. Optimum conditions are determined according to the cells used.

In the present invention, aerobic culture is possible but anaerobic culture is preferred. The bacteria of the genus Bacillus are aerobes or facultative anaerobes and are normally cultured under aerobic conditions with aeration etc. Under such aerobic conditions, saccharides, such as glucose, are metabolized via pyruvic acid in the Krebs cycle. In the present invention, L-lactic acid of high optical purify can be obtained at higher conversion efficiency from pyruvic acid by culturing a microbe of the genus Bacillus under anaerobic conditions. Anaerobic conditions can be maintained by bubbling with carbon dioxide gas or an inert gas (e.g., nitrogen gas, argon gas).

Any conventional method can be used to inoculate the cells to culture media. Also, any conventional method can be used to separate and purify the L-lactic acid produced and the resulting pesticidal toxin that may be obtained concurrently.

According to the first embodiment of the present invention, L-lactic acid can be produced at high optical purities not lower than 70% because the Bacillus strain, which is capable of producing L-lactic acid at optical purities not lower than 70% from assimilable carbon sources and which belongs to *Bacillus anthracis, Bacillus cereus, Bacillus thuringiensis, Bacillus larvae, Bacillus lentimorbus, Bacillus popilliae* or *Bacillus sphaericus*, is cultured. Also, because these strains of the genus Bacillus are less auxotrophic than lactic acid bacteria and can be cultured in inexpensive media, L-lactic acid can be produced at lower costs.

In the third embodiment of the present invention, L-lactic acid can be produced at high optical purities not lower than 95%, because Bacillus sp. SHO-1, capable of producing L-lactic acid at optical purities not lower than 95% from assimilable carbon sources, is cultured. In addition, because Bacillus sp. SHO-1 is less auxotrophic than lactic acid bacteria and *Bacillus coagulans* and can be cultured in inexpensive media, L-lactic acid can be produced at lower costs.

Furthermore, in the second embodiment of the present invention enables the simultaneous production of L-lactic acid at optical purities not lower than 70% and a pesticidal toxin and hence the production of L-lactic acid at lower total at lower total costs, provided that a strain of the genus Bacillus also capable of producing a pesticidal toxin, such as *Bacillus thuringiensis, Bacillus larvae, Bacillus lentimorbus, Bacillus popilliae* or *Bacillus sphaericus*, is cultured.

EXAMPLES

The present invention is hereinafter described in more detail by means of the following examples.

EXAMPLE 1

*Bacillus cereus* JCM 2152 was cultured in Brain Heart Infusion Medium (produced by Becton Dickinson) at 34° C. for 10 hours to yield a seed culture. A 0.1 ml portion of this seed culture was inoculated to 10 ml of liquid medium in two test tubes. The liquid medium, containing 10 g/l peptone (Polypeptone S produced by Nihon Pharmaceutical), 20 g/l glucose and 35 g/l dipotassium phosphate, was adjusted to pH 7.0 with 1M HCl.

Each test tube was stoppered with a porous silicone stopper which permits gas passage; anaerobic culture was conducted in one test tube and aerobic culture in the other as described below.

<Anaerobic culture>

The test tube was placed in BBK GasPak (produced by Becton Dickinson) and subjected to standing culture at 34° C. for 10 hours. Because this culture was conducted in GasPak, the degree of anaerobic state was higher than that in the shaking culture described below.

<Aerobic culture>

The test tube was subjected to shaking culture at 34° C. and 120 rpm for 10 hours without being placed in BBK GasPak (produced by Becton Dickinson).

After cultivation, lactic acid production (g/l), glucose consumption (g/l), conversion rate (%) and optical purity (%) were determined as described below.

<Lactic acid production and glucose consumption>

Lactic acid production and glucose consumption, based on lactic acid concentration (g/l) and glucose consumption (g/l) in the culture broth, respectively, were determined by high performance liquid chromatography (HPLC) under the conditions shown below. Lactic acid production is the sum of the amounts of L- and D-isomers produced.

HPLC: LC-6A (produced by Shimadzu Corporation)

Detector: Differential refractometer (RID-6A, produced by Shimadzu Corporation)

Column: Shim-pack SCR-101H (produced by Shimadzu Corporation)

Column temperature: 60° C.

Eluent: 2.5 mmol aqueous solution of perchloric acid

Flow rate: 0.9 ml/min

<Conversion rate>

Conversion rate is calculated using the following equation:

$$\frac{\text{Conversion}}{\text{rate (\%)}} = \frac{\text{Lactic acid production (g/l)}}{\text{Glucose consumption (g/l)}} \times 100$$

where lactic acid production is the sum of the amounts of L- and D-isomers produced.

<Optical purity>

The optical purity of L-lactic acid is calculated using the following equation:

$$\text{Optical purity (\%)} = 100 \times (L-D)/(L+D)$$

where L is L-lactic acid concentration and D is D-lactic acid concentration.

A culture broth sample was filtered through a UF membrane (UFPI, MILLIPORE) to remove molecules not lower than 5000 in molecular weight. The filtrate was assayed by high performance liquid chromatography to determine the L- and D-lactic acid concentrations in the culture broth.

HPLC: LC-6A (produced by Shimadzu Corporation)

Detector: Spectrophotometer (SPD-6AV, produced by Shimadzu Corporation)
Column: CRS10W (produced by Mitsubishi Chemical)
Column temperature: 30° C.
Detection wavelength: 254 nm
Eluent: 2 mM $CuSO_4$
Flow rate: 0.5 ml/min

EXAMPLE 2

In place of Bacillus cereus JCM 2152 (strain used in Example 1), Bacillus thuringlensis subsp. kurustaki ATCC 33679 was cultured in the same manner as in Example 1, and lactic acid production (g/l), glucose consumption (g/l), conversion rate (%) and optical purity (%) were determined.

COMPARATIVE EXAMPLE 1

In place of Bacillus cereus JCM 2152 (strain used in Example 1), Bacillus coagulans JCM 2257 was cultured in the same manner as in Example 1, and lactic acid production (g/l), glucose consumption (g/l), conversion rate (%) and optical purity (%) were determined.

COMPARATIVE EXAMPLE 2

In place of Bacillus cereus JCM 2152 (strain used in Example 1), Bacillus subtilis JCM 1465 was cultured in the same manner as in Example 1, and lactic acid production (g/l), glucose consumption (g/l), conversion rate (%) and optical purity (%) were determined.

The results of Examples 1 and 2 and Comparative Examples 1 and 2 are shown in Table 1.

TABLE 1

Lactic Acid Produced Using Glucose + Peptone Medium and its Optical Purity

| Bacterial Strain | Lactic acid (g/l) | Glucose Consumption (g/l) | Conversion Rate (%) | Optical Purity (%) |
| --- | --- | --- | --- | --- |
| Standing Culture (Anaerobic) | | | | |
| [Example 1] B. cereus | 13.5 | 13.3 | 98.5 | 98.8 |
| [Example 2] B. thuringiensis | 10.2 | 12.0 | 85.0 | 96.8 |
| [Comparative Example 1] B. coagulans | 0.0 | 0.0 | — | — |
| [Comparative Example 2] B. subtilis | 0.1 | 0.4 | 25.0 | 86.1 |
| Shaking Culture (Aerobic) | | | | |
| [Example 1] B. cereus | 11.9 | 18.2 | 65.4 | 98.2 |
| [Example 2] B. thuringiensis | 11.9 | 19.1 | 62.3 | 97.6 |
| [Comparative Example 1] B. coagulans | 0.7 | 2.2 | 31.8 | 67.9 |
| [Comparative Example 2] B. subtilis | 3.7 | 7.5 | 49.3 | 94.4 |

As shown in Table 1, L-lactic acid was produced at higher conversion rates and higher optical purities when the strain used was Bacillus cereus or Bacillus thuringiensis. Also, higher conversion rates and higher optical purities were obtained in anaerobic culture than in aerobic culture. On the other hand, when the strain used was Bacillus coagulans, a lower amount of lactic acid was produced, with an optical purity lower than 70%, even in aerobic culture. In anaerobic culture, no lactic acid was produced. When the strain used was Bacillus subtilis, lactic acid was produced under both anaerobic and aerobic conditions but its concentrations and conversion rates were 0.1 g/l and 25.0% and 3.7 g/l and 49.3%, respectively. These levels are unsatisfactory for practical application.

It should be noted that nothing more than peptone is necessary as a non-glucose side starting material; this is almost impossible in the case of lactic acid bacteria. In other words, these Bacillus cereus and Bacillus thuringiensis strains are less auxotrophic than lactic acid bacteria and Bacillus coagulans and permit the use of any medium as long as it contains glucose and peptone, demonstrating that they enable L-lactic acid production at higher optical purities using less expensive media.

EXAMPLE 3

Bacillus thuringiensis subsp. kurustaki ATCC 33679 was cultured in a medium comprising 10 g/l peptone (Polypeptone S produced by Nihon Pharmaceutical), 5 g/l ammonium phosphate and 100 g/l glucose, using a 500 ml incubator (volume of culture broth: 500 ml) at 30° C. with 60 rpm stirring, while the pH was kept at 7.0 with 6M caustic soda. During the 15-hour cultivation at 30° C., nitrogen gas was fed at 30 ml/min to maintain anaerobic conditions. The lactic acid concentration in the culture broth was 98 g/l, the optical purity being 99.5%.

From this culture broth, cells were harvested by centrifugation (20,000 G, 15 minutes), resulting in the obtainment of 30 g of cells (wet weight); phase contrast microscopy revealed 0.6×2μ fusiform crystals.

The cells, disrupted for 10 minutes using a 150 W ultrasonic disrupter, were fed to 20 fall webworm larvae. Seven larvae died within 1 hour, 10 within 1 to 2 hours, and 3 within 2 to 5 hours.

In short, when the strain used was Bacillus thuringiensis, L-lactic acid was obtained at high conversion rates and high optical purities, with concurrent obtainment of a pesticidal toxin. These results demonstrate that L-lactic acid can be produced at lower total costs.

EXAMPLE 4

Bacillus sp. SHO-1 was isolated as described below.

Cow's milk was streaked on a BCP count plate agar (produced by Nissui Pharmaceutical) and cultured in a BBL GasPak at 34° C. for 24 hours. Of the growing colonies, one with acid production made the color of the surrounding agar change from purple to yellow, owing to the color change of bromocresol purple contained therein. This colony was taken using a platinum loop and again streaked on a fresh BCP count plate agar. This procedure was repeated 5 cycles. The colony thus screened was inoculated to 10 ml of a medium containing 2% glucose, 1% yeast extract, 1% peptone and 3.5% dipotassium phosphate (adjusted to pH 7.0 with 1M HCl), and cultured in a GasPak at 34° C. for 24 hours. The resulting culture broth was analyzed to select a microbe showing L-lactic acid production at high optical purity.

The Bacillus sp. SHO-1 (FERM BP-5682) strain was thus obtained.

EXAMPLE 5

Bacillus sp. SHO-1 was cultured in a Brain Heart Infusion Medium (produced by Becton Dickinson) at 34° C. for 10 hours to yield a seed culture. A 0.1 ml portion of this seed culture was inoculated to 10 ml of a liquid medium in two test tubes. The liquid medium, containing 10 g/l peptone (Polypeptone S produced by Nihon Pharmaceutical), 20 g/l glucose and 35 g/l dipotassium phosphate, was adjusted to pH 7.0 with 1M HCl.

Each test tube was stoppered with a porous silicone stopper which permits gas passage; anaerobic culture was conducted in one test tube and aerobic culture in the other as described in Example 1.

COMPARATIVE EXAMPLE 3

In place of Bacillus sp. SHO-1 (strain used in Example 5), *Bacillus coagulans* JCM 2257 was cultured in the same manner as in Example 5, and lactic acid production (g/l), glucose consumption (g/l), conversion rate (%) and optical purity (%) were determined.

The results of Example 5 and Comparative Example 3 are shown in Table 2.

TABLE 2

Lactic Acid Produced Using Glucose + Peptone Medium and its Optical Purity

| Bacterial Strain | Lactic acid (g/l) | Glucose Consumption (g/l) | Conversion Rate (%) | Optical Purity (%) |
|---|---|---|---|---|
| *Standing Culture (Anaerobic)* | | | | |
| [Example 5] B. sp. SHO-1 | 16.0 | 16.4 | 97.6 | 99.0 |
| [Comparative Example 3] B. coagulans | 0.0 | 0.0 | — | — |
| *Shaking Culture (Aerobic)* | | | | |
| [Example 5] B. sp. SHO-1 | 14.3 | 20.0 | 71.5 | 98.5 |
| [Comparative Example 3] B. coagulans | 0.7 | 2.2 | 31.8 | 67.9 |

As shown in Table 2, L-lactic acid was produced at high conversion rates and high optical purities in Example 5, in which the strain used was Bacillus sp. SHO-1. Also, higher conversion rates and higher optical purities were obtained in anaerobic culture than in aerobic culture. On the other hand, in Comparative Example 3 where the strain used was *Bacillus coagulans*, a lower amount of lactic acid was produced, with an optical purity lower than 70%, even in aerobic culture. In anaerobic culture, no lactic acid was produced.

Regarding the results in Example 5, it should be noted that nothing more than peptone is necessary as a non-glucose side starting material; this is almost impossible in the case of lactic acid bacteria. In other words, the Bacillus sp. SHO-1 strain is less auxotrophic than lactic acid bacteria and *Bacillus coagulans* and permit the use of any medium, demonstrating that it enables L-lactic acid production at higher purities using less expensive media.

EXAMPLE 6

Bacillus sp. SHO-1 was cultured in a medium comprising 10 g/l peptone (Polypeptone S produced by Nihon Pharmaceutical), 5 g/l ammonium phosphate and 100 g/l glucose, using a 500 ml incubator (volume of culture broth: 500 ml) at 30° C. with stirring at 60 rpm, while the pH was kept at 7.0 with 6M caustic soda. During the 15-hour cultivation at 30° C., nitrogen gas was fed at 30 ml/min to maintain anaerobic conditions. The lactic acid concentration in the culture broth was 97 g/l, the optical purity being 99.9%.

The present invention being thus described, it will be obvious that the same may be varied in many ways. Such variations are not to be regarded as a departure from the spirit and scope of the invention, and all such modifications as would be obvious to one skilled n the art are intended to be included within the scope of the following claims.

What is claimed is:

1. A method for producing L-lactic acid, comprising the steps of:
   (a) cultivating a microorganism capable of producing L-lactic acid from an assimilable carbon source; and
   (b) collecting lactic acid which is at least 70% L-lactic acid from the culture; wherein the microorganism is *Bacillus cereus, Bacillus thuringiensis* or Bacillus sp. SHO-1 (FERM BP-5682).

2. The method according to claim 1, wherein the assimilable carbon source is at least one selected from the group consisting of glucose, sucrose, maltose, fructose, lactose, mannitol, and starch.

3. The method according to claim 1, wherein the cultivation of step (a) is carried out under anaerobic conditions.

* * * * *